United States Patent [19]

Moulder et al.

[11] Patent Number: 5,019,775

[45] Date of Patent: May 28, 1991

[54] CALIBRATING AN EDDY-CURRENT-PROBE USING A MODULATED THERMAL ENERGY SOURCE

[75] Inventors: John C. Moulder; James H. Rose, both of Ames, Iowa

[73] Assignee: Iowa State University Research Foundation, Inc., Ames, Iowa

[21] Appl. No.: 510,112

[22] Filed: Apr. 17, 1990

Related U.S. Application Data

[63] Continuation of Ser. No. 383,801, Jul. 21, 1989, Pat. No. 4,950,990.

[51] Int. Cl.⁵ .................................................. G01R 35/00
[52] U.S. Cl. ........................................ 324/202; 73/1 R
[58] Field of Search .................. 324/202, 224, 226; 73/1 R; 364/571.01, 571.07

[56] References Cited

U.S. PATENT DOCUMENTS

| | | | |
|---|---|---|---|
| 2,855,565 | 10/1958 | Enders | 324/40 |
| 2,989,691 | 6/1961 | Cook | 324/34 |
| 2,989,693 | 6/1961 | Foerster | 324/40 |
| 3,222,917 | 12/1965 | Roth | 73/15 |
| 3,582,772 | 6/1968 | Hammer | 324/40 |
| 3,718,855 | 2/1973 | Rogel et al. | 324/37 |
| 4,064,452 | 12/1977 | Toth | 324/202 |
| 4,425,545 | 1/1984 | Scalese | 324/202 |
| 4,578,643 | 3/1986 | Junker et al. | 324/207 |
| 4,632,561 | 12/1986 | Rosencwaig et al. | 356/432 |
| 4,644,271 | 2/1987 | Toth et al. | 324/238 |
| 4,950,990 | 8/1990 | Moulder et al. | 324/224 |

*Primary Examiner*—Walter E. Snow
*Attorney, Agent, or Firm*—Zarley, McKee, Thomte, Voorhees, & Sease

[57] ABSTRACT

A system for photoinductive imaging for flaw detection of materials and for calibrating eddy-current probes includes positioning an eddy-current probe adjacent to a specimen to be analyzed or to be used as a calibration fixture. A source of thermal energy is modulated and focused to a localized area on the specimen. Thermal energy is then scanned across at least a portion of the detection area of the eddy-probe. The resulting signal from the eddy-current probe is recorded and can depict either thermal-influenced components of the specimen or the response pattern of the eddy-current probe. The record can therefore be used to image flaws or physical holes or shapes of the specimen or calibrate the eddy-current probe.

2 Claims, 5 Drawing Sheets

2MHz PROBE 1 mm 100 kHz

Fig. 6A
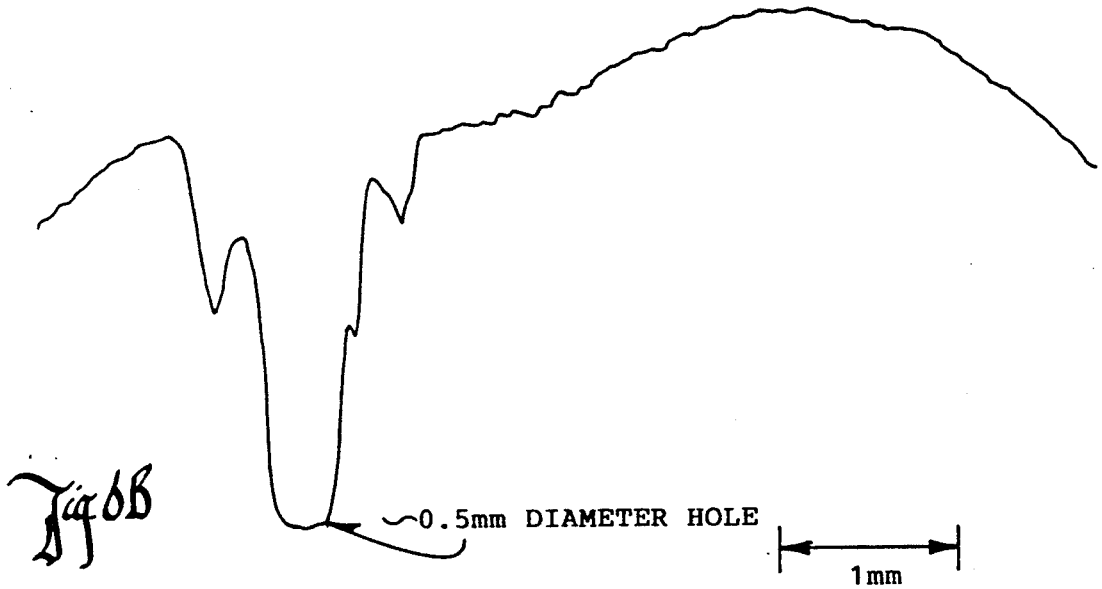
Fig. 6B  ⌒0.5mm DIAMETER HOLE
|←— 1mm —→|

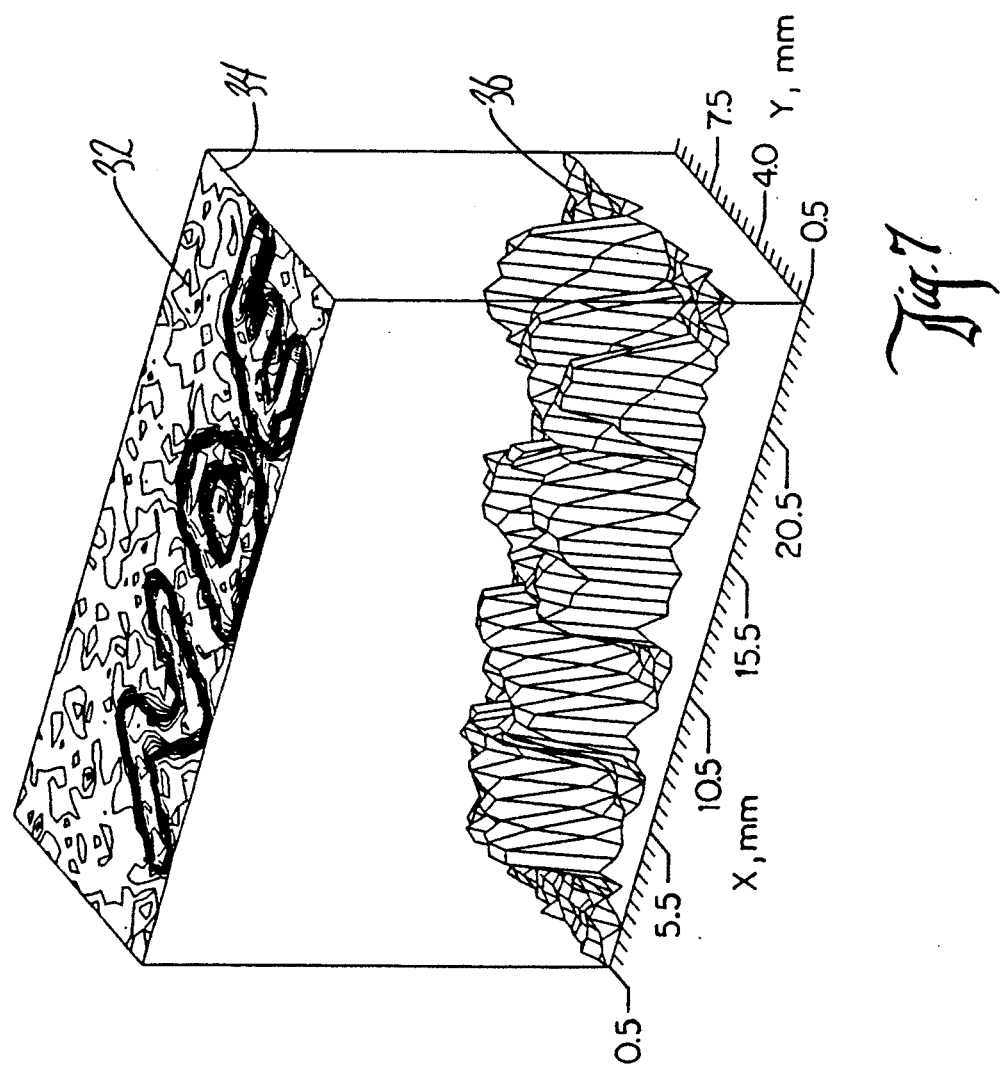

CALIBRATING AN EDDY-CURRENT-PROBE USING A MODULATED THERMAL ENERGY SOURCE

RELATED APPLICATION

This is a continuation of co-pending application Ser. No. 07/383,801 filed on Jul. 21, 1989, now U.S. Pat. No. 4,950,990.

FIELD OF THE INVENTION

The present invention relates to the photoinductive imaging, and in particular, to the use of eddy-current probes and thermal-waves to image a specimen or a response pattern for an eddy-current probe.

PROBLEMS IN THE ART

Eddy-current probes have been used as a form of nondestructive evaluation (NDE). By monitoring the change in inductance of the eddy-current probe as it is scanned over material, information regarding the structure of the material can be derived. Eddy-current probes are valuable because they are noncontacting, can be relatively small in size, and are relatively inexpensive. The major limitations for such probes are that they can only be used with conductive materials and their information is reliable only for near surface regions or thin plates. Also, the spatial resolution of eddy current probes is limited by the size of the probe.

Eddy-current probes, however, have poor reproducibility in probe behavior from probe to probe. Additionally, it is generally necessary to have access to a large number of different sized, shaped, constructed, and operating probes for various tasks. For example, a different probe would be needed for different frequencies of operation. A further example is the need for a larger probe for a larger area of investigation.

A real need therefore exists with respect to calibrating eddy-current probes. However, there is no known easy and efficient method which can be used for various types of eddy-current probe. The present conventional method for calibration involves utilizing what are called "artifact standards" (i.e., parts that contain simulated flaws) made for each type of flaw, material, or geometrical configuration that must be inspected. Therefore, a wide variety of these artifact standards must be maintained, characterized, and inventoried, which is time consuming and expensive.

It is therefore an object of the present invention to provide a means for photoinductive imaging which can be easily and efficiently employed to calibrate eddy-current probes.

It is a further object of the present invention to provide a means and method as above described which can be used for a variety of different size, shape, constructed, and operating eddy-current probes.

Another object of the present invention is to provide a means and method as above described which can image the characteristic response pattern of an eddy current probe.

A further object of the present invention is to provide a means and method as above described which is nondestructive, and can be economically and efficiently incorporated into instrumentation. Eddy-current probes are widely known to be used for NDE flaw detection. It has been found that photoinductive imaging also has application to flaw detection which may represent an improvement over utilizing solely eddy-current probe detection. By utilizing photoinductive imaging, it is possible to improve the spatial resolution capabilities above that of eddy current probes alone.

It is therefore a further object of the present invention to provide a means and method for photoinductive imaging which allows for nondestructive evaluation of materials with good resolution.

A further object of the present invention is to provide a means and method as above described which is useful in flaw detection of materials.

These and other objects, features, and advantages of the present invention will become more apparent with reference to the accompanying specification and claims.

SUMMARY OF THE INVENTION

The present invention is related to a means and method of photoinductive imaging for conductive materials, generally as to near surface layers of the materials or to thin plate or sheet materials or thin conductive films on non-conducting or partially-conducting substrates. The means and method of the present invention are useful in calibrating eddy-current probes, mapping the response of eddy-current probes, or for nondestructive imaging of materials for use in, for example, flaw detection.

An eddy-current probe is positioned adjacent to the specimen. The specimen can either be one which is to be analyzed or imaged, or can be a flaw-free control specimen used for calibration purposes. In the case of calibration of the probe, the probe and specimen can remain stationary while a source of localized heating is raster scanned on the opposite side of the specimen to create localized thermal waves and heating in the specimen coincident with the probe.

Reading of the eddy-current probe are then recorded over time to create a map or image of the variation of eddy-current probe electrical impedance with respect to the raster scan.

This procedure creates basically an image or map of the response pattern for the particular probe. By viewing the response pattern, characteristics of the probe can be discerned and the probe can be calibrated.

With regard to imaging of the specimen, the eddy-current probe and localized heating source are raster scanned across the specimen. Alternatively, the specimen and eddy current probe can remain stationary while the localized heating source is raster scanned across the specimen. The output of the eddy-current probe is then recorded to produce an image of that portion of the specimen which was raster scanned. Because any flaws in the material will result in variations in temperature change as compared to portions of the material that are not flawed, the image will produce a map of that portion of the specimen showing, with good positional resolution, location of the flaw such as occlusions, holes, cracks, and the like.

BRIEF DESCRIPTION OF THE DRAWINGS

FIG. 3a showing the image of magnitude of the eddy-current probe versus time; FIG. 3b showing the image of phase shift versus time.

FIGS. 6a an 6b are depictions of an actual raster scan on a specimen with a hole, FIG. 6a scanning the specimen location without the hole; FIG. 6b representing a scan across the location of the hole.

FIG. 7 is a perspective representation of a photoinductive image produced according to the present invention.

DETAILED DESCRIPTION OF THE PREFERRED EMBODIMENT

Figure 1:
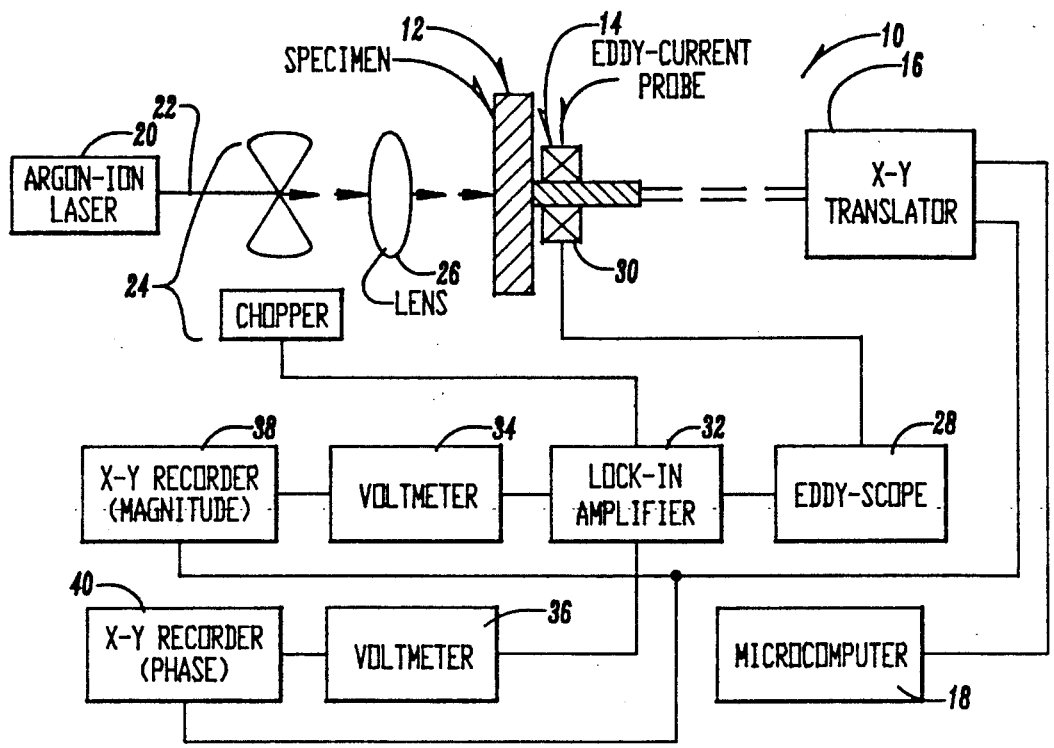
FIG. 1 is a schematic view of one embodiment of a system for photoinductive imaging.

To assist in an understanding of the invention, a preferred embodiment of the present invention will now be described with reference to the drawings. Reference numerals will be utilized to indicate components or features in the drawings.

Referring specifically to FIG. 1, a photoinductive imaging system 10 is shown schematically. A specimen 12, comprised of a thin sheet of conductive material such as metal foil, is positioned adjacent an eddy-current probe 14 such as are well known in the art. The eddy-current probe 14, in this embodiment, and specimen 12, are positioned in a holder, such as is well within the skill of those of ordinary skill in the art, which in turn is connected to an X-Y translator 16. Translator 16 serves to move probe 14 and specimen 12 according to instructions from a microcomputer 18.

An argon-ion laser 20 produces a beam 22 which passes through a chopper mechanism 24. The chopper mechanism 24, such as is known in the art, basically pulses the laser through a lens 26, which serves to focus beam 22 onto specimen 12. A very localized or small area of specimen 12 is therefore impacted directly by beam 22 creating thermal waves which heat up specimen 12 at that localized area, penetrating to a depth dependent on the chopping frequency.

Chopper 24 is controllable for various frequencies and modulates beam 22 of laser 20.

An eddy-scope, such as is well known in the art, is connected to the coil 30 of eddy-current probe 14. Eddy-scope 28 is in turn connected to lock in amplifier 32. The lock in amplifier 32 is synchronized to chopper 24.

The signal from the eddy-scope 28 analyzed by the lock-in amplifier 32 results in a magnitude component and a phase component. Each of these components is sent to separate volt meters 34 and 36 respectively from lock in amplifier 32. The analog output signals of volt meters 34 and 36 are summed with a signal from a vertical position sensor and fed to the vertical channels of x-y recorders 38 and 40 such as a linear variable differential transformer (lvdt). The horizontal channels of x-y recorders 38 and 40 are fed with a signal from a horizontal position sensor. The signal at x-y recorders 38 and 40 presents the modulation of the impedance of the eddy-current probe 14 and is synchronized with the chopped laser beam 22. The signal also represents an image of the sample at the location of probe 14.

The x-y translator 16 moves the combined probe and specimen in a computer-controlled manner through the beam 22. It is to be understood that this movement could be in any reasonable manner, but conventionally is a raster-scanned so that a reliable and discernible image can be obtained.

Figure 2:
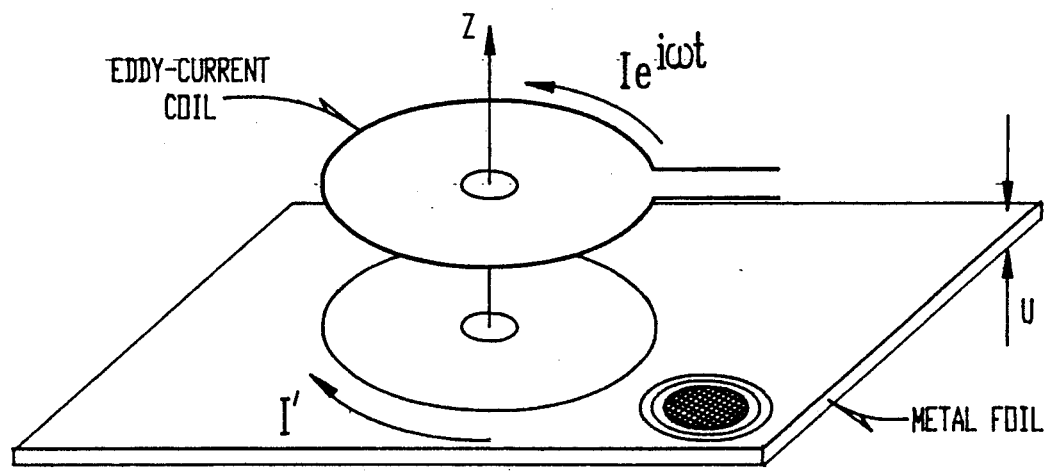
FIG. 2 is a diagrammatic representation of the process of photoinductive imaging.

FIG. 2 diagrammatically depicts the specifics of the photoinductive imaging method using the system 10 of FIG. 1. Thermal wales are generated in specimen 12 (metal foil) by focusing the modulated laser beam 22 on one side of specimen 12 causing localized temperature-induced fluctuations in the specimen 12's conductivity. These fluctuations are synchronously detected with an eddy-current probe 14 placed on the opposite side of specimen 12. It is to be understood, however, that the probe could be positioned on the same side of specimen 12. Both the thermal diffusion length and the electromagnetic skin depth are large compared to specimen 12 thickness. Raster scanning of beam 22 across specimen 12 allows photoinductive imaging of thermally absorpting features on specimen 12. This includes black marks on the surface of specimen 12, as will be discussed with regard to FIGS. 3a–3d, or small holes in the specimen 12 as will be discussed with regard to FIGS. 5 and 6a–6b. Eddy-current signals offer excellent spatial resolution whereas thermal waves can enhance this resolution and utilize the simple, small, non-contact eddy-current detectors. Improved detectability of flaws such as surface-smeared cracks can be achieved.

Figure 3A:
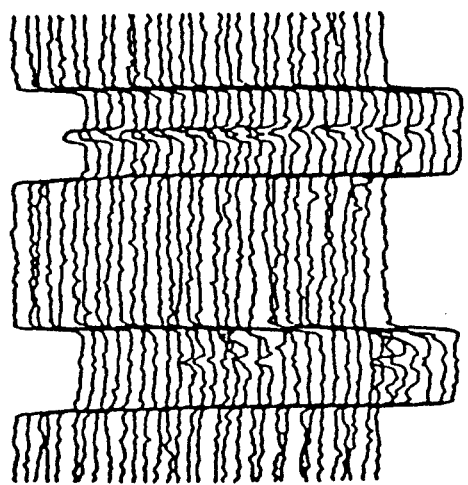
FIGS. 3a–3d relates to photoinductive imaging of two blackened strips positioned upon an aluminum specimen (FIGS. 3c and 3d)
Figure 3B:
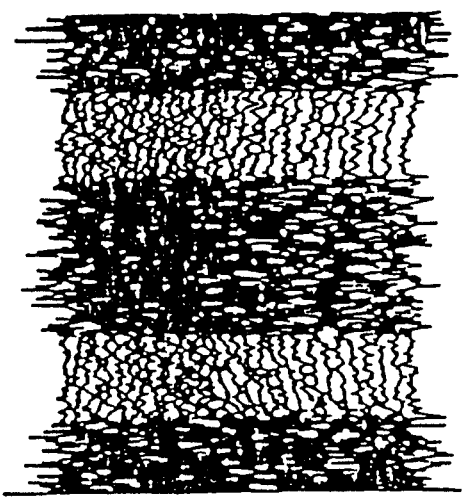

FIGS 3a and 3b show the magnitude and phase images obtained when a nominal one watt laser beam 22, focused on a 30 micrometer ($\mu$m) diameter spot is raster scanned across an aluminum foil specimen 12 (20 $\mu$m thick) which has two black ink strips on its surface (see FIG. 3a and 3d) to simulate the presence of a flaw structure. The black regions cause increased laser heating similar to what occurs in the presence of flaws such as voids.

FIG. 3a shows the magnitude image signal increases in the black regions corresponding to a temperature induced resistivity increase resulting in a higher eddy-current probe 14 impedance. The dip structure in the magnitude image at the center of the left strip is due to a bare metal region.

The phase image contrast of FIG. 3b is believed to be primarily due to a noise reduction mechanism. The images were acquired with laser modulation and eddy-current probe frequencies of 13 hertz (Hz) and 100 kilohertz (kHz) respectively resulting in the thermal-wave decay length and electromagnetic skin depth being considerably larger than the sample thickness of 20 $\mu$m. This specimen was fixed to the eddy-current probe during imaging and the laser beam raster scanned across the specimen.

Figure 3C:
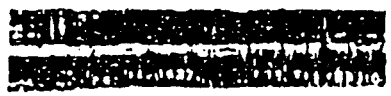
Figure 3D:
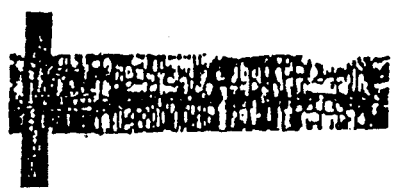

The length of the black bar in FIGS. 3c and 3d is 1 mm. The lock in amplifier 32 sensitivity was 6 mV with a time constant of 125 ms.

It is to be understood that system 10 could operate by either moving the specimen and probe in combination with respect to laser beam 22, or scanning the beam 22 across the fixed specimen and probe. In either case, the images of FIGS. 3a and 3b are possible because the sensitive area of the probe 14 was considerably larger than the image area.

Figure 5:
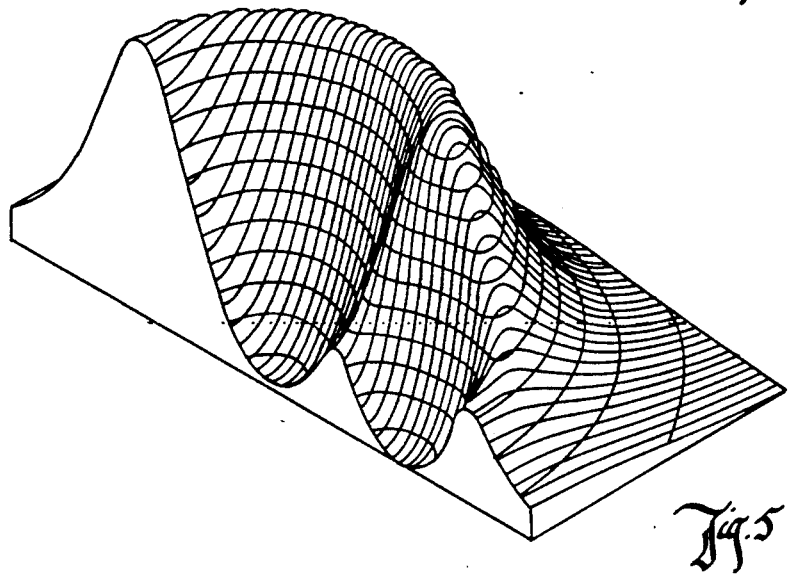
FIG. 5 is a theoretical representation of photoinductive imaging for a thin sheet specimen having a small hole.

By referring to FIGS. 5, and 6a and 6b, another imaging capacity of the present invention is depicted. FIG. 5 depicts a theoretical calculation of the signal for an aluminum foil specimen having a small hole directly under a single turned coil of an eddy-current probe, with the laser beam 22 scanned across the foil specimen. The outline of the small hole can clearly be seen.

FIG. 6a shows a single line of the raster scan through a portion of the specimen away from the hole. FIG. 6b then shows a single line scan directly through the hole. FIG. 6b shows the sharp edges of the hole depicting the high resolution of the present invention. The structure in the signal at the edges of the hole, which is uneven, is believed to be caused by scratches in the ink coating from the needle that was used to make the hole.

Resolution is believed to be better than eddy-current probe detection alone. In eddy-current imaging, the resolution is dominated by the size of the probe. In the present invention, utilizing photoinductive imaging, the resolution is governed by the size of the thermal spot or, as in this case, by the diameter of the laser focal spot. In the imaging of FIGS. 6a and 6b, the foil specimen was blackened to improve adsorption of the laser energy.

FIG. 7 shows in composite form a gold film 32 which was deposited on a layer of glass 34. The letters "NDE" in outline form were written on top of the gold film as shown in FIG. 7.

By utilizing the imaging capability of the present invention, the three dimensional photoinductive image 36, shown underneath plate 34 in the diagrammatic view of FIG. 7, was derived. As can be seen, the black ink, as with the black strips in FIGS. 3A-D, alter the conductivity measurements as the probe and localized heating spot were scanned across plate 34. The three dimensional images of the letters "NDE" are clearly shown in image 36.

It can therefore be seen that the present invention can be useful in imaging thermally absorbing features or voids or flaws or cracks. It is also believed that the present system is applicable to not only very thin sheets or foils, but could also be used with thicker materials.

The capability for imaging was also found to have valuable applicability to calibrating or mapping the response of eddy-current probes.

Similar to the photoinductive imaging discussed above, to calibrate a current-eddy probe, the system of 10 of FIG. 1 is utilized. Instead of a specimen to be analyzed, the specimen 12 consists of a calibration fixture. The calibration fixture can be, for example, thin plates of the same material the probe will be used to inspect, curved fixtures if the probe is designed to inspect holes such as bolt holes, or fixtures made from specially sensitive material such as magnetic materials near a phase transition or semiconducting materials, or metals with a large temperature coefficient of conductivity, if that is the use to which the probe is to be put. Additionally, special fixtures could be designed to mimic the geometry the probe in intended to inspect.

The localized heating source, again such as laser beam 22 would then be operated to induce a small, localized region of changed conductivity in the calibration fixture. This region of perturbed conductivity is then scanned over the fixture while recording the variation in eddy-current probe 14's electrical impedance, producing a map of the probe's response pattern. The response pattern is then used for calibration purposes, or for other uses.

Figure 4A:
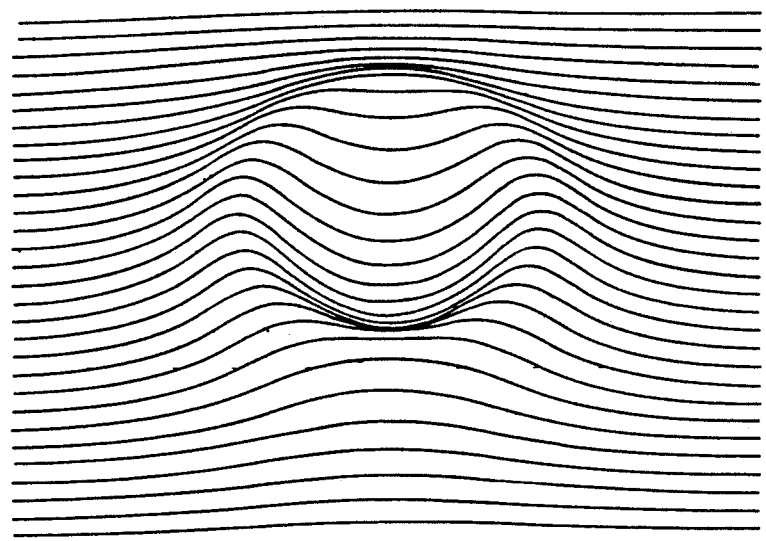
FIGS. 4a and 4b represent photoinductive imaging of the response pattern for two different eddy-current probes.
Figure 4B:
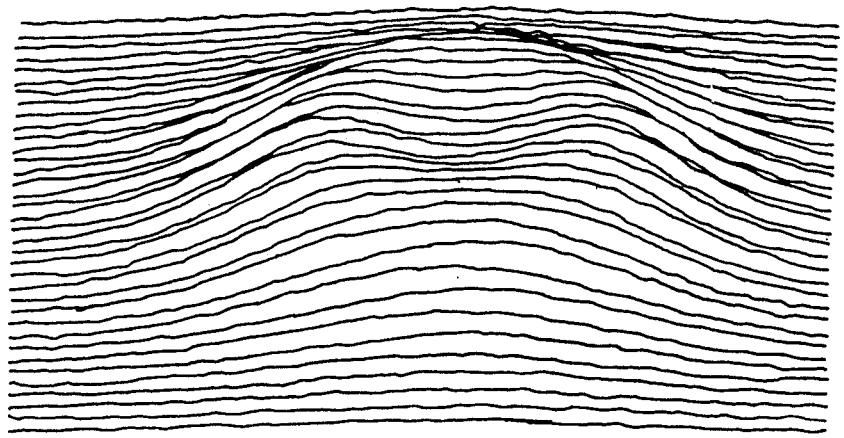

FIGS. 4a and 4b depict two maps of response patterns for two different eddy-current probes. FIG. 4a shows the response pattern for a two megahertz (MHz) probe, whereas FIG. 4b shows the pattern for a 100 kilohertz (kHz) probe. The patterns directly characterize each probe. As can be seen by comparing FIGS. 4a and 4b, the maximum strength of response and the shape of the pattern are clearly distinguishable. This is useful in selecting a probe for a particular use.

It is to be understood that a response pattern can be used to calibrate the probe or to analyze probe quality. Probe quality can be assessed by translating or rotating the probe with respect to the calibration fixture.

The probe's magnetic field (its fundamental physical characteristic) can also be determined quantitatively from the response pattern.

The photoinductive images of the response pattern for the probes in FIGS. 4a and 4b show the characteristic circular-shaped pattern expected for the current distribution in the conductive calibration fixture, which mirrors the pattern of the magnetic field. From patterns such as FIGS. 4a and 4b, information relevant to probe calibration could be obtained such as follows.

For example, the symmetry of the pattern can reveal any tilting or defects in the probe construction. The relative vertical displacement of the pattern is proportional to the probe's field strength; so greater vertical displacement indicates a stronger field, or more sensitive probe. The actual quantitative strength of the probe's magnetic field per unit excitation current could also be obtained from the vertical displacement.

It will be appreciated that the present invention can take many forms and embodiments. The true essence and spirit of this invention are defined in the appended claims, and it is not intended that the embodiment of the invention presented herein should limit the scope thereof.

For example, localized changes in the conductivity of the specimen or calibration fixture can be easily created by a variety of means. Examples include, but are not limited to, laser beams, focused electromagnetic radiation (even an ordinary beam of light from an incandescent light source), electron or other particle beams, or x-ray beams can be used to locally heat the surface which in turn causes the change in the local conductivity. Thick parts or specimens can also be scanned by using an equipment configuration such that the eddy current probe and the laser beam are incident form the same side.

Hot spot localization can be affected by modulating the heat input to the specimen or calibration fixture. In the preferred embodiment, a chopper was used to modulate the laser beam. For certain heat sources, modulation can be accomplished with electrical pulses rather than a chopper, or by an acoustic optic modulator, as is well known in the art. Other methods are possible. It is to be understood that careful selection of the modulation frequency limits the size of the hot spot to a size much less than the size of the probe, which is important.

An optional enhancement would be to connect a CRT to display the image or probe map. Another option would be to add controls to vary the frequency of operation and to adjust the sensitivity of the display. The system could also have connection means for easy communication of the probes to the system by having different plug-in modules or the like.

It is to be again appreciated that for different applications, and for different considerations, the source of heat (such as a laser beam) and the probe measuring conductants can be positioned on opposite sides of the specimen, or they can be on the same side. FIGS. 1 and 2 show them on opposite sides. However, both could be on the same side, for example, when used on thicker materials, by utilizing conductivity probe which can accommodate the source of heat to be directed to the specimen within its operable field range. An example would be a coil with a number of turns whereby a sufficient gap exists or could be created between two turns to allow passage of a focused laser beam or some other type of narrowed heat source.

An example of another type of narrowed heat source would be the use of fiber optics to direct energy such as a laser beam to a localized area of the specimen. Fiber optics could be used instead of a lens to narrow the width and localize the heat source. As is well known in the art, an optical fiber coupler could receive the chopped laser beam and channel it into a fiber optic which could physically pass through the probe, such as an eddy current probe, and direct the laser beam to the specimen.

It is further to be understood that the present application does apply not only to unitary specimens such as conductive plates or sheets or thicker conductive materials, but also to conductive films fixed to non-conducting or partially conducting substrates, such as the gold film upon the glass plate as shown in FIG. 7.

For the preferred embodiment of the invention shown in FIG. 1, it is to be understood that a variety of types of instruments and components could be used. For example, a heating source could be an argon-ion laser available from Spectra Physics, Mountain View, Calif. under product model 2010; the beam chopper could be a HMS light beam chopper, model 222 from Ithaco, Ithaca, N.Y. The lens to focus the laser beam could be any simple positive lens; and preferably a microscope objective to get a small spot size.

The eddy scope could be such as is available under model NDT-19 from Nortec of Kennewick, Wash.; and the eddy current probe also could be obtained from Nortec.

The x-y translator, such as is known in the art, could be a daedal roller bearing translator table and can be computer controlled. The x-y recorders are available from companies such as Hewlett Packard. The lock-up amplifiers could be model 5206 from EG&G/Princeton Applied Research, Princeton, N.J. Volt meters are such as is well known in the art. The microcomputer could be any general type of microcomputer such as an IBM PC.

An example of how the present invention can improve upon methods such as using solely eddy current probes is with respect to detecting smear cracks. It is to be understood that cracks smeared by grinding or peening basically short circuit eddy currents which reduces signal strength and thus reduces the accuracy and reliability of detection using solely eddy current probes. With the present method, the heating source such as the laser heats the specimen over the crack to a greater extent then the surrounding area. This produces greater signal strength.

What is claimed is:

1. A method of mapping the response pattern of an eddy-current probe comprising:

positioning a calibration fixture of previously known characteristics adjacent to an eddy-current probe means having a detection area;

generating a modulated thermal source;

directing the modulated thermal source onto the calibration fixture at a localized area on the fixture;

scanning the localized area across the fixture coincident with at least the detection area of the probe means;

detecting with the probe means changes in the electrical conductivity in the localized scanned area, the changes caused by localized temperature changes in the specimens; and recording the detected changes in electrical conductivity to create a mapping of the response area of the probe.

2. A means for calibrating eddy-current probes comprising:

placement means for holding a calibration fixture relative to an eddy-current probe having a detection area to be calibrated;

thermal energy source means for imposing thermal energy upon a localized area of the calibration fixture;

modulation means for modulating the thermal energy source before imposition upon the calibration fixture;

scanning means for scanning the localized area of modulated thermal energy across at least the detection area of the eddy-current probe;

receiver means for receiving the signal from the eddy-current probe relating to changes in electrical conductivity in the localized areas scanned by the modulated thermal energy source; and recording means for recording the detected changes in electrical conductivity to create a map of the response pattern for the eddy-current probe.

* * * * *